United States Patent [19]

Lê Van Mao et al.

[11] Patent Number: 4,698,452
[45] Date of Patent: Oct. 6, 1987

[54] ETHYLENE LIGHT OLEFINS FROM ETHANOL

[75] Inventors: Raymond Lê Van Mao; Le H. Dao, both of Montreal, Canada

[73] Assignee: Institut Nationale de la Recherche Scientifique, Sainte-Foy, Canada

[21] Appl. No.: 914,295

[22] Filed: Oct. 2, 1986

[51] Int. Cl.$^4$ ............................ C07C 1/20; C07C 1/24
[52] U.S. Cl. ................................................... 585/640
[58] Field of Search ....................... 585/640, 639, 651

[56] References Cited

U.S. PATENT DOCUMENTS

| | | | |
|---|---|---|---|
| 4,025,575 | 5/1977 | Chang et al. | 585/640 |
| 4,052,479 | 10/1977 | Chang et al. | 585/640 |
| 4,134,926 | 1/1979 | Tsao et al. | 585/640 |
| 4,247,731 | 1/1981 | Wunder et al. | 585/640 |
| 4,278,565 | 7/1981 | Chen et al. | 585/640 |
| 4,511,667 | 4/1985 | Le Van Mao et al. | 502/64 |
| 4,615,995 | 10/1986 | Le Van Mao | 502/64 |

FOREIGN PATENT DOCUMENTS

| | | | |
|---|---|---|---|
| 1186345 | 4/1985 | Canada | 585/640 |
| 0105591 | 4/1984 | European Pat. Off. | 585/640 |

OTHER PUBLICATIONS

Ondejans et al., Applied Catalysis, vol. 3, pp. 109-115 (1982).
Le Van Mao et al, Canadian Journal of Chemical Engineering, vol. 64(3); p. 462 (1986).
Le Van Mao et al, Canadian Journal of Chemical Engineering; vol. 64, p. 514 (1986).

Primary Examiner—Asok Pal
Attorney, Agent, or Firm—Robic, Robic & Associates

[57] ABSTRACT

Ethylene, other light olefins and gasoline are produced from ethanol, or a mixture of ethanol/light alcohols or water over a pentasil-type zeolite into which zinc and manganese are preferably incorporated. The ethylene yield is linearly proportional to the ethanol content in the feed. No ethers and only insignificant amounts of light parafins are produced.

13 Claims, 2 Drawing Figures

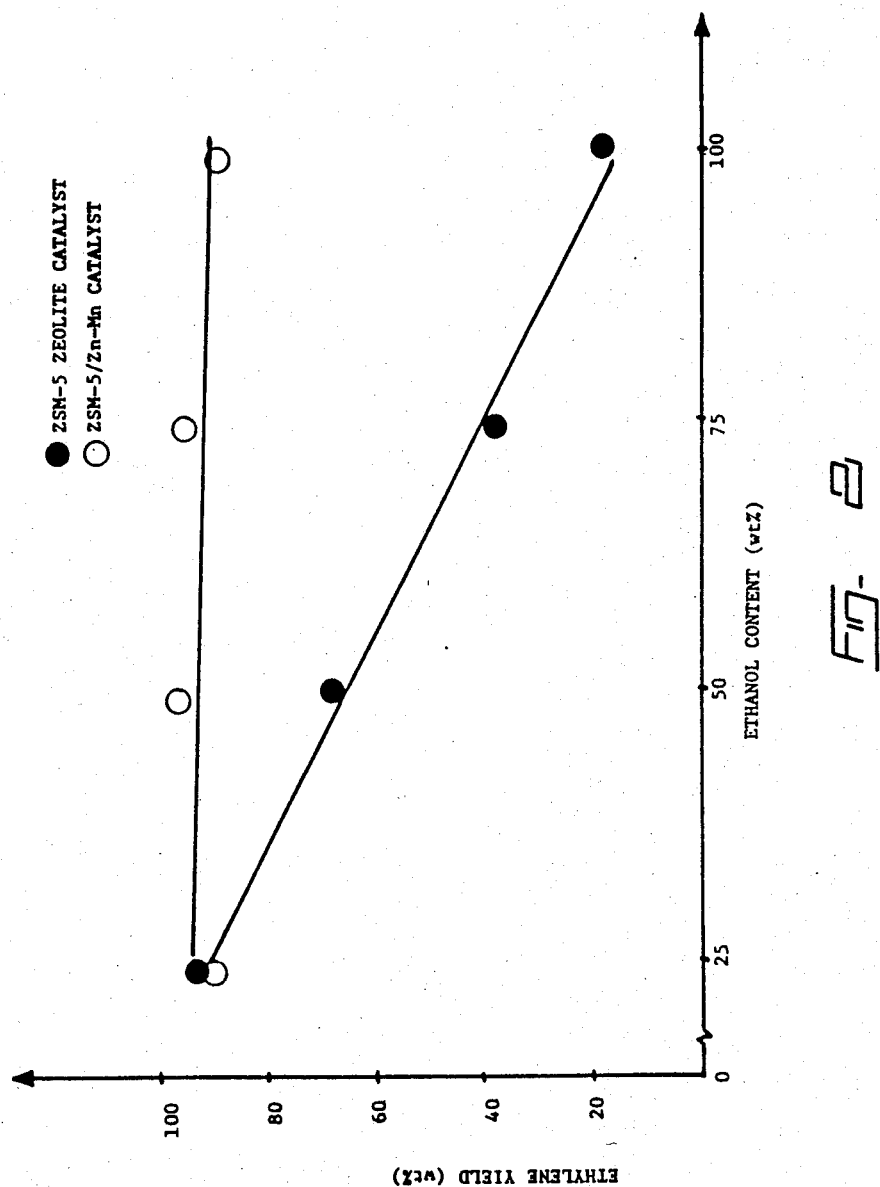

ETHYLENE LIGHT OLEFINS FROM ETHANOL

1. DESCRIPTION OF THE INVENTION

This invention relates to a novel process for the conversion of ethanol or its mixtures with light alcohols and optionally water into hydrocarbons with specific and unusual selectivity towards ethylene. More particularly, the present invention relates to the use of ZSM-5 zeolite based catalysts into which Zn alone or Zn and Mn are incorporated.

The silica-rich ZSM-5 zeolite and its homologue, the ZSM-11 zeolite, belong to the crystalline aluminosilicate pentasil family. Their peculiar catalytic properties are mainly due to their regular framework with a pore size which is intermediate to the large pore sized zeolites (for instance, zeolites X and Y) and the small pore sized zeolites (for instance the A zeolite). The shape selectivity of the pentasil zeolites is the catalytic expression of many factors. Such factors if referred to the methanol conversion into hydrocarbons can be inexhaustively listed as follows: (a) the sieving effect, i.e. the capability of the zeolite to admit into its pores or to reject reactant molecules according to their critical diameters; (b) the (reverse) sieving effect, i.e. the capability of the zeolite to allow the product molecules to diffuse out of its pores, thus in the case of a too bulky product molecule, the latter is forced to undergo an additional cracking into shorter molecules before diffusing out; (c) the effect on the reaction intermediates, i.e. the capability of certain active sites to determine the length and geometry of reaction intermediate species. This is exactly the case with the (acid) sites located at the zeolite channel intersection which sites are responsible for the formation of aromatics in the final products. The high Si/Al ratio of the pentasil zeolites is also an advantage in terms of thermal stability and resistance to acid media. These zeolites exhibit also very strong acidity which in the methanol reaction promotes the formation of longer hydrocarbons from light olefinic precursors (propylene and ethylene). Thanks to the "narrowness" of the zeolite channels, no reaction products having more than 11 carbon atoms are formed. The temperature normally used for the methanol reaction ranges from 300° C. to 500° C., preferably from 350° C. to 450° C. The ZSM-5 zeolite used for such a reaction is under acid or H-form: i.e. that nearly all the sodium ions originally present in the zeolite as synthesized have been exchanged for protons. Several techniques for ion-exchanging with protons are available. Two possible techniques are firstly sodium-proton direct exchange in the presence of a dilute acid (usually HCl) solution; and secondly sodium-$NH_4$ exchange (in the presence of an ammonium salt containing solution) followed by an activation at elevated temperature in order to decompose the ammonium ions into gaseous $NH_3$ and a proton which is thus left on the zeolite active site.

According to the scientific literature, the (H-form) ZSM-5 zeolites when reacted with light alcohols (including therefore methanol and ethanol) give very similar product distributions. These results are in perfect agreement with theoretical mechanistic studies which identify an identical first reaction step leading to olefinic precursors (namely propylene and ethylene). On the other hand, certain conventional zeolites like zeolites A, X and Y exhibit dehydrating properties with respect to propanol and higher alcohols (to produce olefins as primary reaction products and ethers as secondary reaction products—the ethers are usually formed in very significant amounts [U.S. Pat. No. 3,529,033, V. J. Frilette and P. B. Weisz (1970)] at relatively low temperatures (200° F.–650° F.). The difference between these zeolites and the normal silica-gel dehydrating catalyst is their (the zeolites') high selectivity towards linear alcohols; moreover calcium-A zeolite was claimed to be the most efficient catalyst for such dehydration reactions.

According to the prior art, the ethanol conversion over alumina led to the corresponding ether; only a very small amount of ethylene is formed. On the other hand, ethanol reacts over certain oxides (such as thorium, chromium or titanium oxides) and produces simultaneously, ethylene and acetaldehyde (a dehydrogenation product). The decomposition of ethanol over supported thoria catalysts produces almost exclusively ethylene, however, the ethanol conversion is very low.

Thus the processes of the prior art either have low product specificity or achieve low yields or both.

The present invention therefore provides a process for producing light olefins in very high yields consisting of sending ethanol or an ethanol containing medium through a modified pentasil-type zeolite catalyst. In a preferred embodiment, the aqueous solution of ethanol is at a concentration of from 2 to 19% by volume.

The key role in the process of the present invention is played by a catalyst which is capable of converting totally ethanol and its mixtures with methanol and/or water into $C_1$–$C_{11}$ hydrocarbons with very high yields of $C_2$–$C_4$ light olefins and of ethylene. In a preferred embodiment the yields of $C_2$–$C_4$ light olefins and of ethylene are linearly proportional to the ethanol content in the ethanol/methanol mixture, the highest values being obtained with pure ethanol (ethylene/propylene ratio by weight: higher than 14). To achieve this unexpected catalytic performance, modified ZSM-5 zeolite catalysts preferably bearing Zn and Mn are used. Comparative tests show that pure unmodified (acid form) ZSM-5 zeolite based catalysts give nearly constant and low yields in light olefins and in ethylene (with an ethylene/propylene ratio by weight lower than 1) with the same feeds and under the same reaction conditions. The preferred ZSM-5/Zn-Mn catalysts used according to the present invention give a product distribution when reacting with propanol, n-butanol or isobutanol, which is very close to the product distribution of the pure methanol conversion.

Thus, the process of the invention has great potential application because of the following prospects:

(a) ethanol can be derived from biomass by a chemical or enzymatic process. It is always convenient to have a second (catalytic) process which is capable of giving high yields of ethylene (up to 99 wt %) and of other commercially valuable hydrocarbons.

(b) ethanol/methanol mixtures or ethanol/methanol/higher alcohols mixtures can be obtained from synthesis gas [for example, the following processes as claimed in: U.S. Pat. No. 4,014,913, M. M. Bhasin et al. (1977) and U.S. Pat. No. 4,122,110, A. Sugier and E. Freund (1978)]. The syngas can be in turn derived from the following sources: natural gases, coal, heavy oils, biomass.

To illustrate the efficiency of the process of the present invention, we report in the following section the preparation, the characterization and the use in the process of the present invention of three catalyst samples: the pure ZSM-5 zeolite based; the ZSM-5/Zn and the ZSM-5/Zn-Mn.

2. PREPARATION AND CHARACTERIZATION OF THE CATALYSTS (a) ZSM-5 sample for comparative test 26 g of silica Baker (dried at 120° C. for 12 hours, ≧90 wt % in silica) were mixed with an aqueous solution containing 40 g of tetrapropylammonium bromide (Fisher), 2.5 g of NaOH dissolved in 140 ml of distilled water. The suspension was heated at 80° C. under vigorous stirring for 1 hour. Then, a solution prepared from 2 g of sodium aluminate (Fisher, % weight composition: alumina=46.79; sodium oxide=28.44) dissolved in 20 ml of distilled water, was added. Heating was continued at 80° C. with vigorous stirring for 10 minutes. The suspension was transferred into a Teflon ® bottle which was then put into a Parr autoclave, and heated for 10 days at 170° C. (±5° C.). After cooling, the suspension was discharged and filtered; the solid was washed with distilled water until the washing liquid had a pH lower than 9 and then dried at 120° C. for 12 hours and activated in the air at 550° C. for 12 hours.

The resulting solid was brought in contact with an aqueous solution of ammonium chloride (5% by weight), using 10 ml of solution per gram of compound. The suspension was heated at 80° C. under reflux condition and with moderate stirring. After 1 hour of heating, the suspension was allowed to settle and the liquid was then rapidly removed. A fresh volume of ammonium chloride solution was added and the suspension was heated again for another hour. The same procedure was repeated several times so that the entire operation lasted 5 hours. The suspension was filtered and the solid was washed until $Cl^-$ ions were no longer present in the washing solution. The compound was dried at 120° C. for 12 hours and activated in the air for 12 hours at 550° C.

The resulting material (acid form or H-form) had the following chemical composition (% by weight): silica=97.0; alumina=2.9 and sodium oxide=0.2 (Si/Al molar ratio=29). Its degree of crystallinity which was determined according to the method of Le Van Mao et al. (Canadian Journal of Chemistry, Vol. 63(12), 3464, 1985, section "X-ray powder diffraction") was DC=100%.

The final catalyst was prepared according to the following procedure: the previously obtained solid was intimately mixed with bentonite (20% by weight) and made into a paste with distilled water, 1 ml of water was used for each gram of the solid. The paste was pressed into 1 mm outside diameter (O.D.) extrudates. Finally, the extrudates were dried at 120° C. for 12 hours and activated in the air at 550° C. for 12 hours. This sample was called "ZSM-5".

(b) ZSM-5/Zn

The Zn loading onto the ZSM-5 zeolite was done according to the following procedure:

13 g of the ZSM-5 zeolite (H-form, powder) were brought in contact with an aqueous solution of $ZnCl_2$ (Mallinckrodt 2% by weight), using 130 ml of solution as total volume of $ZnCl_2$ solution. The suspension was heated at 80° C. under reflux and with moderate stirring. After 3 hours of heating, the suspension was cooled down, then filtered and washed with distilled water until $Cl^-$ ions were no longer present in the washings. The compound was dried at 120° C. for 12 hours and activated in the air at 550° C. for 12 hours.

The Zn metal content of the solid was 0.37 % by weight.

The final catalyst (extrusion with bentonite) was prepared according to the same procedure as previously described for the ZSM-5 sample.

(c) ZSM-5/Zn-Mn 4 g of the ZSM-5/Zn (powder) were intimately mixed with 0.8 g of bentonite and made into a paste with an aqueous solution of $MnCl_2$ [$MnCl_2 \cdot H_2O$ from Baker, 6% by weight], using 3.8 ml as total volume of $MnCl_2$ solution. The paste was pressed into 1 mm O.D. extrudates. Finally, the extrudates were dried at 120° C. for 12 hours and activated in the air at 550° C. for 12 hours. This sample was called "Zsm-5/Zn-Mn" and its Mn content was 1.17 wt %.

3. DETAILED DESCRIPTION OF THE INVENTION

The obtained samples [under bead form, density=0.50 g/cubic cm] were used in the following reaction systems.

Catalytic runs were performed by injecting ethanol, methanol or their mixtures, or higher alcohols or aqueous solutions of ethanol using an injection syringe on an infusion pump into an alcohol vaporizer-gas mixer. Nitrogen gas was supplied to the alcohol feed vaporizer and gas mixer from a cylinder connected in-line with a flowmeter. The vaporized alcohol feed was then carried by the nitrogen gas through a catalyst bed set in a catalytic reactor contained inside an oven which was thermo-regulated. A chromel-alumel thermocouple was placed in the catalyst bed and was used, in conjunction with a digital thermometer unit, to monitor the temperature of the catalyst bed. The gaseous mixture flowing out of the reactor was run through a series of condensers maintained at 5°-10° C., to a liquid collector immersed in an ice ath followed by a cylinder from which gas sampling was carried out.

Following a pre-run of 10 minutes, the liquid products were collected and the gaseous ones were analysed periodically by gas chromatography (GC) using a 5 m long column packed with Chromosorb P ® coated with 20 % by weight of Squalane ® connected in series with a 2.5 m long column packed with Carbopack ® graphite coated with picric acid (0.19 % by weight). The GC used was a dual FID Hewlett-Packard Model 5790 equipped with a 3392A Model integrator. It was equipped also with a capillary column (length 50 m; PONA ® type fused silica coated with a cross-linked polymer) which was used for accurate analyses of the liquid fractions after a complete run. The composition of the aqueous layer was also determined by GC using a methanol in water calibration standard curve.

The preferred reaction conditions used in the experiments were as follows: temperature=300°-450° C. (most preferred 400° C.); catalyst weight=4 g; total pressure=1 atm; alcohol or aqueous ethanol pressure=0.9 atm; inert gas (stripping gas)=nitrogen; weight hourly space velocity (W.H.S.V.)=2.4 $h^{-1}$; duration of a run=4 hours.

For each sample, three catalytic runs were performed with the same alcohol feed. The reported conversions and product distributions were averaged values of data from these runs. Reaction temperatures and flow rates were carefully and automatically controlled. As a consequence, no variation in the catalytic data higher than 5% was observed with the same catalyst tested under the same reaction conditions.

BRIEF DESCRIPTION OF DRAWINGS

Process results are reported in Tables 1, 2, 3, 4, 5 and 6.

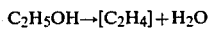

$$C_2H_5OH \rightarrow [C_2H_4] + H_2O$$

Figure 1:
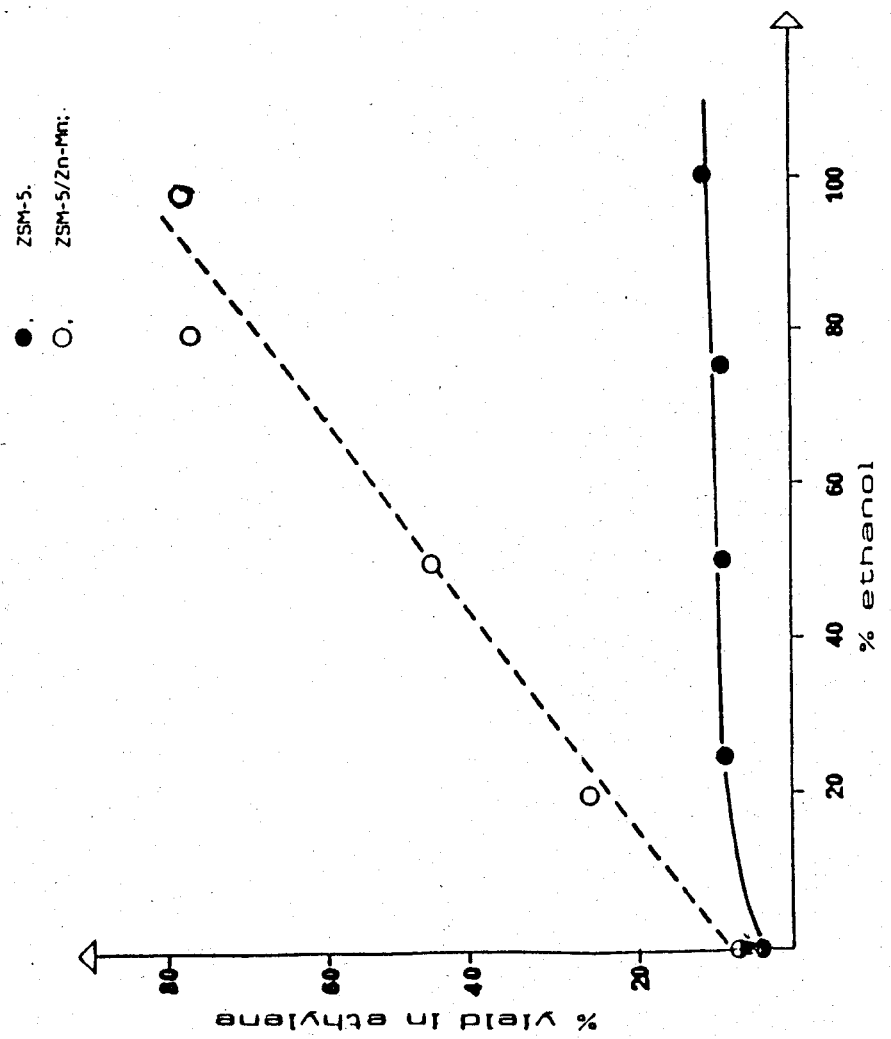
in FIG. 1 which graphically illustrates one embodiment of the present invention, viz ethylene yield versus ethanol content in the methanol-ethanol mixture using the ZSM-5/Zn-Mn catalyst (clear circles) and using the ZSM-5 catalyst (black circles); and in FIG. 2 which graphically illustrates another embodiment of the invention viz: ethylene yield versus ethanol content in the aqueous solution. Note that in FIG. 2 the ethylene yield is that with respect to the maximum theoretical yield in hydrocarbons according to the equation.

Table 1 reports the data of conversion and product selectivities obtained by reacting methanol, ethanol and their mixtures at various ethanol contents, over the ZSM-5 sample. This is a comparative test. The following observations should be made:

(a) when the ethanol content varied in the methanol-ethanol feed, the yields in ethylene and light olefins did not vary significantly and remained levelled at 10% and 25-30%, respectively.

(b) the ethylene/propylene weight ratio remained practically unchanged below the value 1.0.

Table 2 reports the data of conversion and product selectivities obtained by reacting methanol, ethanol and mixtures thereof at various ethanol contents, over the ZSM-5/Zn-Mn and the ZSM-5/Zn (pure ethanol only). Several observations should be made:

(a) Zn incorporation by ion-exchange into the ZSM-5 zeolite produced a catalyst which yielded higher amounts of ethylene and light olefins in the ethanol conversion. Incorporation of Mn to the ZSM-5/Zn by dry impregnation led to an additional and significant increase in ethylene and light olefins yields (more than 82 wt % and 94 wt % respectively).

(b) the yields of light olefins and of ethylene observed in the reaction over the ZSM-5/Zn-Mn catalyst of a methanolethanol mixture were linearly proportional to the ethanol content in the feed (see also FIG. 1). The ethylene/propylene weight ratio varied in the same manner and was as high as 14.1 with 100% ethanol in the feed.

Table 3 reports the data of conversion and product selectivities obtained by reaction over the ZSM-5/Zn-Mn of a pure alcohol (methanol, ethanol, propanol, n-butanol and isobutanol).

Only ethanol among the light alcohols tested gave unexpectedly very high yields in light olefins and in ethylene.

Three series of runs were performed with ethanol in aqueous solutions.

Table 4 reports the catalytic data of the previously mentioned catalysts in presence of a 50/50 wt % ethanol-water mixture.

As main results, the selectivity to ethylene increases as follows:

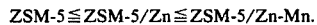

ZSM-5 ≦ ZSM-5/Zn ≦ ZSM-5/Zn-Mn.

Table 5 reports the catalytic data of the ZSM-5/Zn-Mn sample in presence of ethanol-water mixtures with various ethanol concentrations. Thus, the selectivity towards ethylene increases with decreasing ethanol concentration; i.e., at a very low ethanol concentration, the dehydration of ethanol into ethylene prevails.

Table 6 reports the catalytic data of the ZSM-5 catalyst used as reference sample. As also shown by FIG. 2, there is a linear relationship between the ethylene yield and the ethanol content in the aqueous solution: the lower ethanol content, the higher the ethylene yield. With the ZSM-5/Zn-Mn catalyst, the ethylene yield is very high (higher than 90 wt % with respect to the maximum theoretical yield in hydrocarbons) and does not vary significantly with ethanol concentration changes (see FIG. 2 and Table 5).

In all the above processes, no ethers were produced. It is worth nothing that ethers are normally obtained in very significant amounts in the dehydration of light alcohols to olefins over usual catalysts like silica-alumina.

TABLE 1

(COMPARISON TEST)
CONVERSION AND PRODUCT SELECTIVITIES IN PRESENCE OF METHANOL, ETHANOL AND THEIR MIXTURES. CATALYSTS: ZSM-5

| CATALYST | FEED (wt %) | CONVERSION (%) | PRODUCT SELECTIVITIES (%) | | | | | | LIGHT OLEFINS ($C_2$—$C_4$) (%) | LIQUID HYDROCARBONS (%) | ETHYLENE PROPYLENE |
|---|---|---|---|---|---|---|---|---|---|---|---|
| | | | Paraffins ($C_1$—$C_4$) | Ethylene | Propylene | Butenes | Aromatics | Aliphatics | | | |
| ZSM-5 | MeOH (100%) | 99 | 33 | 6 | 10 | 4 | 32 | 15 | 20 | 47 | 0.6 |
| ZSM-5 | MeOH (75%) EtOH (25%) | 99 | 24 | 11 | 14 | 6 | 25 | 20 | 31 | 45 | 0.7 |
| ZSM-5 | MeOH (50%) EtOH (50%) | 99 | 24 | 10 | 13 | 6 | 26 | 21 | 29 | 47 | 0.7 |
| ZSM-5 | MeOH (25%) EtOH (75%) | 99 | 28 | 9 | 11 | 6 | 26 | 20 | 26 | 46 | 0.8 |
| ZSM-5 | EtOH (100%) | 92 | 20 | 11 | 12 | 9 | 20 | 29 | 32 | 49 | 0 |

TABLE 2

CONVERSION AND PRODUCT SELECTIVITIES IN PRESENCE OF METHANOL, ETHANOL AND THEIR MIXTURES. CATALYSTS: ZSM-5/Zn and ZSM-5/Zn—Mn

| CATALYST | FEED (wt %) | CONVERSION (%) | PRODUCT SELECTIVITIES (%) | | | | | | LIGHT OLEFINS ($C_2$—$C_4$) (%) | LIQUID HYDROCARBONS (%) | ETHYLENE PROPYLENE |
|---|---|---|---|---|---|---|---|---|---|---|---|
| | | | Paraffins ($C_1$—$C_4$) | Ethylene | Propylene | Butenes | Aromatics | Aliphatics | | | |
| ZSM-5 (Zn—Mn) | MeOH (100%) | 94 | 11 | 9 | 19 | 14 | 21 | 32 | 42 | 53 | 0.5 |
| ZSM-5 | MeOH (80%) | 97 | 9 | 31 | 15 | 9 | 13 | 24 | 55 | 37 | 2.1 |

TABLE 2-continued

CONVERSION AND PRODUCT SELECTIVITIES IN PRESENCE OF METHANOL, ETHANOL AND THEIR MIXTURES.
CATALYSTS: ZSM-5/Zn and ZSM-5/Zn—Mn

| CATALYST | FEED (wt %) | CON-VERSION (%) | Paraffins ($C_1$—$C_4$) | Ethylene | Pro-pylene | Bu-tenes | Aro-matics | Ali-phatics | LIGHT OLEFINS ($C_2$—$C_4$) (%) | LIQUID HYDRO-CARBONS (%) | ETHYLENE PROPYLENE |
|---|---|---|---|---|---|---|---|---|---|---|---|
| ZSM-5 (Zn—Mn) | EtOH (20%) MeOH (50%) | 98 | 5 | 56 | 12 | 7 | 7 | 14 | 75 | 21 | 4.7 |
| ZSM-5 (Zn—Mn) | MeOH (20%) EtOH (80%) | 99 | 2 | 81 | 9 | 3 | 1 | 4 | 93 | 5 | 9.0 |
| ZSM-5 (Zn—Mn) | EtOH (100%) | 99 | 1 | 82 | 6 | 6 | 0 | 6 | 94 | 6 | 14.1 |
| ZSM-5 (Zn) | EtOH (100%) | 99 | 3 | 69 | 11 | 6 | 3 | 8 | 86 | 11 | 6.3 |

TABLE 3

CONVERSION AND PRODUCT SELECTIVITIES IN PRESENCE OF PURE $C_1$-$C_4$ ALCOHOLS.
CATALYSTS: ZSM-5/Zn—Mn

| CATALYST | FEED (wt %) | CON-VERSION (%) | Paraffins ($C_1$-$C_4$) | Ethylene | Pro-pylene | Bu-tenes | Aro-matics | Ali-phatics | LIGHT OLEFINS ($C_2$-$C_4$) (%) | LIQUID HYDRO-CARBONS (%) | ETHYLENE PROPYLENE |
|---|---|---|---|---|---|---|---|---|---|---|---|
| ZSM-5 (Zn—Mn) | MeOH | 94 | 11 | 9 | 19 | 14 | 21 | 32 | 42 | 53 | 0.40 |
| ZSM-5 (Zn—Mn) | EtOH | 99 | 1 | 82 | 6 | 6 | 0 | 6 | 94 | 6 | — |
| ZSM-5 (Zn—Mn) | P$\eta$OH | 99 | 13 | 3 | 15 | 15 | 18 | 36 | 33 | 54 | 0.33 |
| ZSM-5 (Zn—Mn) | nBuOH | 99 | 16 | 4 | 18 | 11 | 17 | 34 | 33 | 51 | 0.33 |
| ZSM-5 (Zn—Mn) | iBuOH | 99 | 15 | 4 | 18 | 10 | 16 | 37 | 32 | 53 | 0.30 |

TABLE 4

CATALYTIC DATA OF DIFFERENT CATALYST WITH A 50/50 wt % ETHANOL-WATER SOLUTION
[T = 400° C., W.H.S.V. = 2.5 $h^{-1}$]

| CATALYST | ALCOHOL CONVERSION (wt %) TOTAL | to hydrocarbons | Paraffins ($C_1$—$C_4$) | $C_2$—$C_4$ Ethylene | Others | ($C_5$—$C_{11}$) liquid Aliphatics | Aromatics |
|---|---|---|---|---|---|---|---|
| ZSM-5 | 99+ | 93 | 1.6 | 73.5 | 16.9 | 7.6 | 0.4 |
| ZSM-5/Zn | 99+ | 99+ | 0.3 | 90.5 | 5.9 | 3.1 | 0.2 |
| ZSM-5/Zn—Mn | 99+ | 99+ | — | 98.3 | 1.0 | 0.7 | — |

TABLE 5

CATALYTIC DATA OF THE ZSM-5/Zn—Mn CATALYST WITH VARIOUS AQUEOUS SOLUTIONS OF ETHANOL
[T = 400° C., W.H.S.V. = 2.5 $h^{-1}$]

| FEED (wt %) Ethanol | Water | ALCOHOL CONVERSION (wt %) TOTAL | to hydrocarbons | Paraffins ($C_1$—$C_4$) | $C_2$—$C_4$ olefins Ethylene | Others | ($C_5$—$C_{11}$) liquid Aliphatics | Aromatics |
|---|---|---|---|---|---|---|---|---|
| 25 | 75 | 99+ | 93 | — | 97.5 | 0.2 | 0.8 | 1.5 |
| 50 | 50 | 99+ | 99+ | — | 98.3 | 1.0 | 0.7 | — |
| 75 | 25 | 99+ | 99+ | 0.1 | 94.5 | 3.0 | 2.1 | 0.3 |
| 100 | — | 99+ | 99+ | 0.2 | 89.9 | 6.2 | 3.5 | 0.2 |

TABLE 6

Catalytic data of the ZSM-5 sample in presence of various ethanol aqueous solutions.

| Feed (wt %) Ethanol | Water | Ethanol conversion (wt %) Total | To hydrocarbons | $C_1$—$C_4$ paraffins | $C_2$—$C_4$ olefins ethylene | Others | $C_5$—$C_{11}$ liquid Hydrocarbons Aliphatics | Aromatics |
|---|---|---|---|---|---|---|---|---|
| 25 | 75 | 99 | 95 | 0.0 | 98.2 | 0.8 | 0.8 | 0.2 |
| 50 | 50 | 99 | 93 | 1.6 | 73.5 | 16.9 | 7.6 | 0.4 |
| 75 | 25 | 99 | 94 | 8.9 | 40.9 | 28.8 | 17.5 | 3.9 |

TABLE 6-continued

Catalytic data of the ZSM-5 sample in presence of various ethanol aqueous solutions.

| Feed (wt %) | | Ethanol conversion (wt %) | | Product selectivities (wt %) | | | | |
| --- | --- | --- | --- | --- | --- | --- | --- | --- |
| | | | | $C_1$—$C_4$ | $C_2$—$C_4$ olefins | | $C_5$—$C_{11}$ liquid Hydrocarbons | |
| Ethanol | Water | Total | To hydrocarbons | paraffins | ethylene | Others | Aliphatics | Aromatics |
| 100 | — | 99 | 92 | 19.5 | 10.5 | 20.8 | 29.0 | 20.2 |

We claim:

1. A process for producing $C_2$-$C_4$ olefins in yields higher than 94% by weight comprising sending ethanol or an aqueous solution of ethanol as feed over a Mn-Zn modified pentasil-type zeolite catalyst, modified by incorporation of Zn by ion-exchange and subsequent incorporation of Mn by dry impregnation using an aqueous solution of a Mn salt in the presence of bentonite, said process being carried out at a temperature ranging from 300° to 450° C.

2. A process according to claim 1, wherein, using a feed of aqueous ethanol, the $C_2$ to $C_4$ olefin in greatest yield is ethylene, whose yield is at least 90% by weight.

3. A process according to claim 1, wherein the aqueous solution of ethanol is at a concentration of from 2 to 19% by volume.

4. A process according to claim 1, wherein the modified pentasil-type zeolite has a silica/alumina molar ratio of about 29.

5. A process according to claim 1, wherein the modified catalyst comprises 0.37% by weight of Zn and 1.17% by weight of Mn.

6. A process according to claim 1, wherein the process is carried out at a total pressure of about 1 atmosphere.

7. A process according to claim 1, wherein the process is carried out at a temperature of about 400° C.

8. A process for the production of ethylene comprising sending methanol in mixture with ethanol over a Mn-Zn modified pentasil-type zeolite catalyst modified by incorporation of Zn by ion-exchange and subsequent incorporation of Mn by dry impregnation using an aqueous solution of a Mn salt in the presence of bentonite, said process being carried out at a temperature ranging from 300° to 450° C.

9. A process according to claim 8, wherein the yield of ethylene is linearly proportional to the ethanol content of the feed.

10. A process according to claim 8, wherein the process is carried out at a total pressure of about 1 atmosphere.

11. A process according to claim 8, wherein the process is carried out at a temperature of about 400° C.

12. A process according to claim 8, wherein the modified catalyst comprises 0.37% by weight of Zn and 1.17% by weight of Mn.

13. A process according to claim 8, wherein the modified pentasil-type zeolite has a silica/alumina molar ratio of about 29.

* * * * *